US011717180B2

(12) United States Patent
Maki et al.

(10) Patent No.: US 11,717,180 B2
(45) Date of Patent: Aug. 8, 2023

(54) PULMONARY FUNCTION MEASUREMENT DEVICE, PULMONARY FUNCTION MEASUREMENT METHOD, AND PULMONARY FUNCTION MEASUREMENT PROGRAM

(71) Applicant: TERUMO KABUSHIKI KAISHA, Tokyo (JP)

(72) Inventors: Shin Maki, Ebina (JP); Tomoki Utsugida, Machida (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/138,624

(22) Filed: Sep. 21, 2018

(65) Prior Publication Data

US 2019/0125212 A1    May 2, 2019

Related U.S. Application Data

(63) Continuation of application No. PCT/JP2017/009787, filed on Mar. 10, 2017.

(30) Foreign Application Priority Data

Mar. 23, 2016   (JP) .................................. 2016-058365

(51) Int. Cl.
*A61B 5/08*     (2006.01)
*A61B 8/08*     (2006.01)
(Continued)

(52) U.S. Cl.
CPC .............. *A61B 5/0816* (2013.01); *A61B 5/08* (2013.01); *A61B 5/0803* (2013.01); *A61B 5/746* (2013.01);
(Continued)

(58) Field of Classification Search
CPC ....... A61B 5/0816; A61B 5/08; A61B 5/0803; A61B 5/746; A61B 8/00; A61B 8/5207; A61B 8/5223; A61B 8/5269; A61B 5/72
(Continued)

(56) References Cited

U.S. PATENT DOCUMENTS

2002/0151789 A1\* 10/2002 Mansy .................... A61B 8/485
                                                                        600/431
2006/0070623 A1\* 4/2006 Wilkinson ............... A61B 8/08
                                                                        128/204.23
(Continued)

FOREIGN PATENT DOCUMENTS

JP    2002509747 A    4/2002
JP    2010534548 A    11/2010

OTHER PUBLICATIONS

International Search Report (PCT/ISA/210) dated Jun. 6, 2017, by the Japanese Patent Office as the International Searching Authority for International Application No. PCT/JP2017/009787.
(Continued)

*Primary Examiner* — Christian Jang
*Assistant Examiner* — Mitchell E Alter
(74) *Attorney, Agent, or Firm* — Buchanan Ingersoll & Rooney PC

(57) ABSTRACT

A pulmonary function measurement device, a pulmonary function measurement method, and a pulmonary function measurement program are provided which are non-invasive and can operate with a reduced burden on a measurement subject. The pulmonary function measurement device for measuring data for evaluating a pulmonary function includes a sound output unit that is capable of being fixed to a part of a body surface near ribs, and outputs a sound toward the ribs; a sound detection unit that is capable of being fixed to a part of a body surface near the ribs toward which the sound is to be output, and detects a sound that is transmitted from the
(Continued)

sound output unit through the ribs; and an attenuation calculation unit that calculates an acoustic attenuation from information on the sound output by the sound output unit and the sound detected by the sound detection unit.

20 Claims, 5 Drawing Sheets

(51) Int. Cl.
*A61B 8/00* (2006.01)
*A61B 5/00* (2006.01)
(52) U.S. Cl.
CPC .............. *A61B 8/00* (2013.01); *A61B 8/5207* (2013.01); *A61B 8/5223* (2013.01); *A61B 8/5269* (2013.01); *A61B 5/72* (2013.01)
(58) Field of Classification Search
USPC ......................................................... 600/529
See application file for complete search history.

(56) References Cited

U.S. PATENT DOCUMENTS

2007/0118056 A1* 5/2007 Wang .................... A61B 5/1117
600/595
2009/0036777 A1 2/2009 Zhang et al.
2013/0018240 A1 1/2013 Mccoy

OTHER PUBLICATIONS

Written Opinion (PCT/ISA/237) dated Jun. 6, 2017, by the Japanese Patent Office as the International Searching Authority for International Application No. PCT/JP2017/009787.
An English Translation of the International Search Report (Form PCT/ISA/210) and the Written Opinion of the International Searching Authority (Form PCT/ISA/237) dated Jun. 6, 2017, by the Japanese Patent Office in corresponding International Application No. PCT/JP2017/009787. (6 pages).

* cited by examiner

PULMONARY FUNCTION MEASUREMENT DEVICE, PULMONARY FUNCTION MEASUREMENT METHOD, AND PULMONARY FUNCTION MEASUREMENT PROGRAM

CROSS-REFERENCES TO RELATED APPLICATIONS

This application is a continuation of International Application No. PCT/JP2017/009787 filed on Mar. 10, 2017, which claims priority to Japanese Application No. 2016-058365 filed on Mar. 23, 2016, the entire content of both of which is incorporated herein by reference.

FIELD OF THE INVENTION

The present disclosure generally relates to a pulmonary function measurement device, a pulmonary function measurement method, and a pulmonary function measurement program, which are for measuring data for evaluating a pulmonary function.

BACKGROUND DISCUSSION

When the cardiac output decreases due to insufficient action of the heart, a mechanism of the living body for maintaining the cardiac output works to suppress the decrease in the cardiac output. However, burdens are placed on various portions of the body, and as a result, a symptom may appear. Heart failure is not a disease name, but indicates such a "state of the body generated as a result of insufficient action of the heart."

When heart failure occurs, a cardiac pump function is decreased, so that blood cannot be sent out sufficiently. Therefore, the blood that cannot be sent out from the heart is accumulated in an organ immediately before the heart in the circulation system, so that a symptom appears. In the case of a right heart failure, a symptom appears in the general circulation system, and in the case of a left heart failure, a symptom appears in the pulmonary circulation system. In the case of the left heart failure, the blood that flows from the lungs to the left heart is stagnated in the lungs, so that the liquid component of the blood in the lungs oozes out (i.e., seeps) into lung tissue, and the lungs become a congested state.

It is difficult to be aware of symptoms of a heart failure. Accordingly, an occurrence of an acute exacerbation such as a myocardial infarction brings the awareness of the heart failure for the first time. Therefore, there is a demand for a method that can rather easily monitor a heart failure and can help identify heart failure at a relatively early stage.

For this purpose, various devices that measure the state of the lungs have been proposed. For example, JP-T-2010-534548 (the term "JP-T" as used herein means a published Japanese translation of a PCT application) describes a device that outputs a sound toward lungs for evaluating a cardiac function, and receives the reflected sound, thereby measuring a state of the lungs.

The device described in JP-T-2010-534548 needs to be embedded in a body, has a relatively high invasiveness, and places an increased burden on a measurement subject.

SUMMARY

A pulmonary function measurement device, a pulmonary function measurement method, and a pulmonary function measurement program are disclosed that are non-invasive and can operate with a relatively reduced burden on a measurement subject.

A pulmonary function measurement device is disclosed for measuring data for evaluating a pulmonary function, the pulmonary function measurement device including: a sound output unit configured to be fixed to a part of a body surface near ribs, and outputs a sound toward the ribs; a sound detection unit configured to be fixed to a part of the body surface near the ribs toward which the sound is to be output, and to detect a sound that is transmitted from the sound output unit through the ribs; and an attenuation calculation unit configured to calculate an acoustic attenuation from information on the sound output by the sound output unit and the sound detected by the sound detection unit.

A pulmonary function measurement method is disclosed for measuring data for evaluating a pulmonary function, the pulmonary function measurement method including: outputting a sound from a part of a body surface near ribs toward the ribs; detecting a sound that is transmitted through the ribs from a part of the body surface near the ribs toward which the sound is output; and calculating an acoustic attenuation from information on the output sound and the detected sound.

A pulmonary function measurement program stored in a non-transitory, tangible computer readable recording medium configured to be executable by a computer to measure data for evaluating a pulmonary function is disclosed; the pulmonary function measurement program including: causing a sound output unit to output a sound toward ribs; receiving a detection result from a sound detection unit that detects a sound; and calculating an acoustic attenuation from information on the output sound and the detected sound.

The pulmonary function measurement device, the pulmonary function measurement method, and the pulmonary function measurement program as described above can observe acoustic attenuations in ribs, which serve as an index of the decrease in a pulmonary function, using the sound transmitted through the ribs adjacent to the lung, and thus are relatively non-invasive and can operate with a relatively reduced burden on the measurement subject.

DETAILED DESCRIPTION

Figure 1:
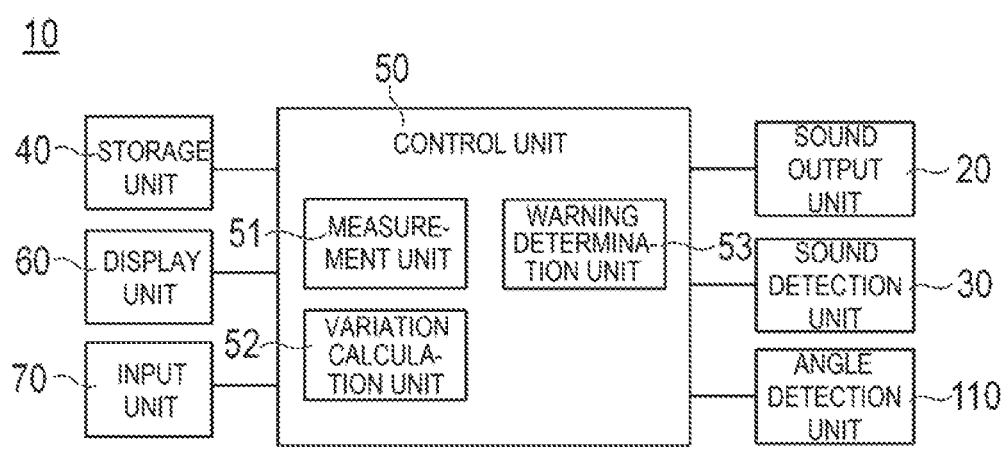
FIG. 1 is a block diagram illustrating a pulmonary function measurement device according to an embodiment.

Hereinafter, with reference to the drawings, an embodiment of the disclosure will be described. Note that, the size ratio in the drawings may be exaggerated for convenience of explanation, and may be different from the actual ratio in some cases.

A pulmonary function measurement device 10 according to an embodiment of the disclosure is a device capable of collecting, on a long term basis, attenuations of a sound that is transmitted through ribs and capable of determining the presence or absence of a left heart failure daily, for example. The pulmonary function measurement device 10 can be used by a measurement subject himself/herself, for example, on a daily basis, and can monitor a change in cardiac state on a relatively long term basis. Moreover, the pulmonary function measurement device 10 can be also used for a relatively short-term monitoring use in which the presence or absence of a heart failure is determined according to an instruction by a doctor during a period of about two or three days to allow a diagnosis with relatively high accuracy in a short time on arrival at the hospital. In the present description, a "front side" of a body means the side where a face is oriented, and a "rear side" of the body means the side where a back is oriented. Note that, the pulmonary function measurement device 10 according to the present embodiment can measure a pulmonary function with the objective of evaluating a cardiac function, but may measure the state of the lungs (the degree of congestion) without the objective of evaluating a cardiac function.

Figure 2:
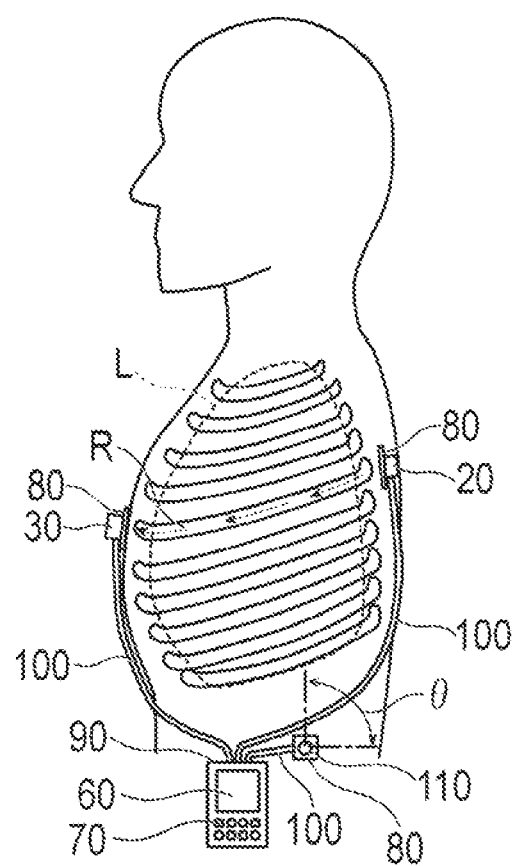
FIG. 2 is a side view illustrating a state where the pulmonary function measurement device is attached to a measurement subject.
Figure 3:
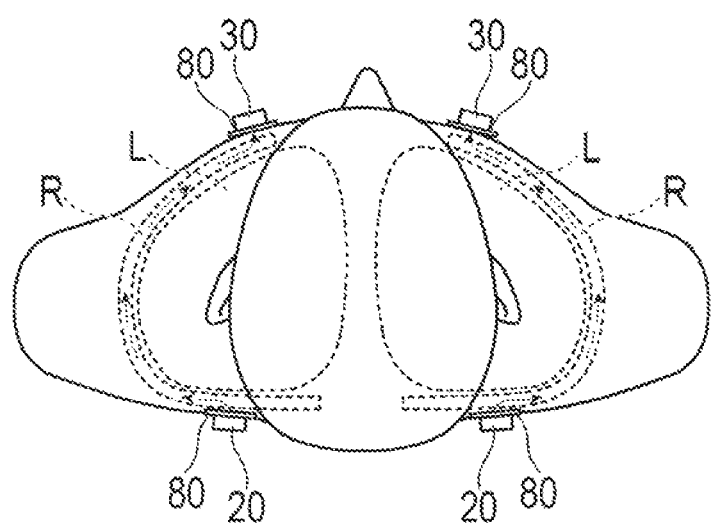
FIG. 3 is a top view illustrating a state where the pulmonary function measurement device is attached to the measurement subject.

The pulmonary function measurement device 10 includes, as illustrated in FIGS. 1 to 3, a sound output unit 20 that outputs a sound, a sound detection unit 30 that detects a sound, a storage unit 40, a control unit 50, an input unit 70, a display unit 60, and an angle detection unit 110. The pulmonary function measurement device 10 is further provided with a fixing member 80 for fixing the sound output unit 20, the sound detection unit 30, and the angle detection unit 110 to a body surface, a device main body 90 that contains the storage unit 40, the control unit 50, the input unit 70, and the display unit 60, and a cable 100 that connects the sound output unit 20, the sound detection unit 30, and the angle detection unit 110 to the housing (i.e., device main body) 90. The control unit 50 and the storage unit (i.e., memory) 40 can form a computer for executing a program to measure data for evaluating a pulmonary function as disclosed. Accordingly, an operation of the pulmonary function measurement device 10 can be executed by the program on the control unit 50 and the storage unit 40.

The sound output unit 20 is a speaker including an oscillator for outputting a sound and an amplifier. The sound output from the sound output unit 20 is used for calculating an acoustic attenuation V (the degree of attenuation) in a rib R. The sound output unit 20 is fixed (i.e., attached) to a side in front of or behind the lung (a side behind the lung in the present embodiment) using the fixing member 80. The fixing member 80 can be, for example, an adhesive tape. The sound output unit 20 is fixed to a part of the body surface near the rib R that is selected for measuring the attenuation. In accordance with an exemplary embodiment, two sound output units 20 corresponding to left and right lungs L are provided. The sound output unit 20 outputs a sound, according to an instruction from the control unit 50, with a sampling period (or specified time) set in advance or input from the input unit 70, a plurality of times within the measurement time (for example, one day). The sampling period during when sounds are output is, for example, 0.1 second to 1 second, although not particularly limited. The sound output unit 20 outputs a time sound set in accordance with the sampling period, for example, a sound is output every 0.1 second to 1 second.

The frequency of the sound output from the sound output unit 20 can be, for example, 100 Hz to 2000 Hz (Hertz), although not particularly limited as long as the sound can pass through the bone. The sound output from the sound output unit 20 may be a single frequency, or may have a predetermined frequency band. Moreover, the sounds output from the two sound output units 20 may have different frequencies, output timings, and the like so as to easily identify for which of the sound output units 20 outputs the sound, from a detection result of the sound.

The sound detection unit 30 can be a microphone for detecting a sound that is transmitted through the rib R from the sound output unit 20. In accordance with an exemplary embodiment, two sound detection units 30 corresponding to the left and right lungs L are provided. The sound detection unit 30 is fixed (i.e., attached) to an opposite side (front side in the present embodiment), out of the front side and the rear side of the lung L, of a side to which the sound output unit 20 is attached, by the fixing member 80. The sound detection unit 30 is fixed to a part of the body surface near the rib R selected for measuring the attenuation. Accordingly, the sound detection unit 30 that is fixed to the front side of the left lung L and the sound output unit 20 that is fixed to the rear side of the left lung L are fixed to different parts of the body surface so as to be near the same left rib R. Moreover, the sound detection unit 30 that is fixed to the front side of the right lung L and the sound output unit 20 that is fixed to the rear side of the right lung L are fixed to different parts of the body surface so as to be near the same right rib R. The sound detection unit 30 transmits a detection result to the measurement unit 51 in a control unit 50.

The sound output unit 20 and the sound detection unit 30 are preferably fixed (i.e., attached) to the same positions on the body surface every time. Note that, the positions to which the sound output unit 20 and the sound detection unit 30 are fixed are not particularly limited as long as the positions are near the same rib R. Accordingly, the positions of the parts of the body surface to which the sound output unit 20 and the sound detection unit 30 are respectively fixed do not need to be positions of the front side and the rear side of the body.

The angle detection unit 110 is a sensor that detects an inclination angle θ of the long axis of the body with respect to the horizontal plane. The angle detection unit 110 transmits a detected signal to the control unit 50 through the cable 100. A position to which the angle detection unit 110 is fixed is not particularly limited as long as the angle detection unit 110 can measure an inclination of the body. The angle detection unit 110 is not particularly limited as long as the angle detection unit 110 can detect the inclination angle θ of the body, and is an acceleration sensor, for example.

The housing (or device main body) 90 is connected to the sound output unit 20, the sound detection unit 30, and the angle detection unit 110 with the cable 100, as illustrated in FIGS. 1 and 2. The device main body 90 is attached to a measurement subject with a belt, for example.

The storage unit (i.e., memory) 40 stores various kinds of operation programs such as a measurement program that is executed in the control unit 50, and various kinds of parameters (for example, thresholds). The storage unit 40 further stores data detected by the sound detection unit 30 and the angle detection unit 110, and data calculated by the control unit 50.

The control unit 50 can include the measurement unit 51, an attenuation calculation unit 52, and a warning determination unit 53. The control unit 50 includes a central processing unit (CPU) and an operation program. The control unit 50 controls in a centralized manner operations of the sound output unit 20, the sound detection unit 30, the angle detection unit 110, the storage unit 40, the measurement unit 51, the attenuation calculation unit 52, the warning determination unit 53, the input unit 70, and the display unit 60.

The measurement unit 51 transmits a signal to the sound output unit 20 to cause the sound output unit 20 to output a sound. The measurement unit 51 receives detection data on the sound from the sound detection unit 30. Upon reception of the detection data on the sound from the sound detection unit 30, the measurement unit 51 specifies the sound output by the sound output unit 20 from the detection data on the sound. For example, the measurement unit 51 can analyze a frequency of the detection data acquired from the sound detection unit 30, and can calculate an amplitude value having a frequency component the same as that of the sound output from the sound output unit 20. The measurement unit 51 divides the amplitude of the sound detected by the sound detection unit 30 by the amplitude of the sound output from the sound output unit 20, thereby obtaining a unit attenuation. Note that, the amplitude of the sound output from the sound output unit 20 is measured in advance and set in the storage unit 40. Accordingly, the measurement unit 51 can read the amplitude of the sound output from the sound output unit 20 from the storage unit 40. Note that, in a case where the sound output unit 20 outputs a sound having a predetermined frequency band, the measurement unit 51 can calculate a unit attenuation in each frequency. In this case, the measurement unit 51 selects a specific frequency with a little noise, and can calculate a unit attenuation in this frequency. Alternatively, the measurement unit 51 calculates unit attenuations in respective frequencies, and can set a mean value of the unit attenuations in each of the respective frequencies as a unit attenuation.

In addition, the measurement unit 51 receives detection data on the inclination angle θ from the angle detection unit 110 when the sound detection unit 30 detects a sound. The measurement unit 51 causes the storage unit 40 to store the unit attenuation (i.e., calculated acoustic attenuation for a sound output by the sound output unit and detected by sound detection unit), the inclination angle θ, and time t when the measurement is performed.

The attenuation calculation unit 52 calculates the attenuation V from data on the unit attenuations recorded during a predetermined measurement time (for example, 24 hours). The attenuation calculation unit 52 calculates a mean value of a plurality of unit attenuations within the measurement time (for example, 24 hours), and determines the attenuation V as the mean value.

Note that, the state of the lungs can depend on the inclination angle θ of the body. For example, the gravity acts in different directions between a standing state (θ=90 degrees) and a lying state (θ=0 degrees), so that the shape of the lungs L changes, and the position of an interstitial fluid also changes. Therefore, when the inclination angle θ of the body is changed, the attenuation V of the rib R that receives a force from the lung L is also changed. Accordingly, the attenuation calculation unit 52 can read out the inclination angle θ with the unit attenuation from the storage unit 40, and can select and average the unit attenuations only in a case where the inclination angle θ satisfies a predetermined condition, which helps enable the attenuation calculation unit 52 to calculate the unit attenuation that is measured with a posture within a predetermined range, and thus to calculate the unit attenuation with relatively high accuracy. The condition for the inclination angle θ is indicated as the following expression (1), for example.

$$45 \text{ degrees} \leq \theta \leq 90 \text{ degrees} \quad \text{expression (1)}$$

When the left cardiac function is decreased, the liquid in the blood vessel of the lungs oozes out (i.e., seeps) into the lung tissue, and the lungs L are congested. When the lungs are congested, a force received by the rib R that surrounds the lungs L from lungs L increases, which suppresses the vibration in the rib R more as the congestion of the lungs L is progressed more, thereby increasing the attenuation of the sound that is transmitted through the rib R. Accordingly, observing the attenuation V of the sound that is transmitted through the rib R makes it possible to observe the degree of the congestion, and as a result, to observe the decrease in the left cardiac function. In other words, as the attenuation V is larger, there is a relatively higher possibility that the cardiac function is abnormal. The attenuation V is calculated for each of the left and right lungs L in the present embodiment.

The warning determination unit 53 compares the attenuation V calculated by the attenuation calculation unit 52 with a threshold. In accordance with an exemplary embodiment, the threshold can be set in advance in the storage unit 40, input from the input unit 70, or calculated from past data, for example. In a case where the attenuation V is larger than the threshold, the warning determination unit 53 determines that the rib R is strongly in contact with the lung L, and the cardiac function (or pulmonary function) is abnormal. In contrast, in a case where the attenuation V is equal to or less than the threshold, the warning determination unit 53 determines that the rib R is not strongly in contact with the lung L, and the cardiac function (or pulmonary function) is normal. The warning determination unit 53 causes the display unit 60 to display a determination result in the case where the warning determination unit 53 determines that the cardiac function is abnormal. Note that, the threshold of the warning determination unit 53 may be, for example, an upper limit value of an average value of most persons, or may be a value obtained by multiplying a mean value of the measurement subject for the past several months by a coefficient.

The warning determination unit 53 can separately determine the two attenuations V corresponding to the left and right lungs L. Moreover, the warning determination unit 53 may perform the determination using a mean value of the attenuations V of both of the lungs L. Moreover, the warning determination unit 53 may separately determine the two attenuations V corresponding to the left and right lungs L, and thereafter may determine that the cardiac function is abnormal in a case where either one of the left and right lungs L is abnormal. Moreover, the warning determination unit 53 may separately determine the two attenuations V corresponding to the left and right lungs L, and thereafter may determine that the cardiac function is abnormal in a case where both of the left and right lungs L are abnormal.

The input unit 70 is a part where a measurement subject performs an input operation. The input unit 70 includes a switch and buttons, for example. Moreover, the input unit 70 may be, for example, a touch panel, a key board, or a mouse. The input unit 70 is used for inputting and resetting of various kinds of parameters (the threshold, the range of the inclination angle, the measure interval, and the determination method), starting and ending of the measurement, selection of a measurement result and a calculation result to be displayed, selection of a graph or a table to be displayed, and other cases.

The display unit 60 is, for example, a display device such as a liquid crystal display (LCD) or an organic electroluminescence (EL) display. The display unit 60 may be, for example, a touch panel that also serves as the input unit 70. The display unit 60 can display on the display unit 60, a value input into the input unit 70, a measurement result, a calculation result, a determination result, or the like as a character, a numerical value, a table, or a graph.

Figure 4:
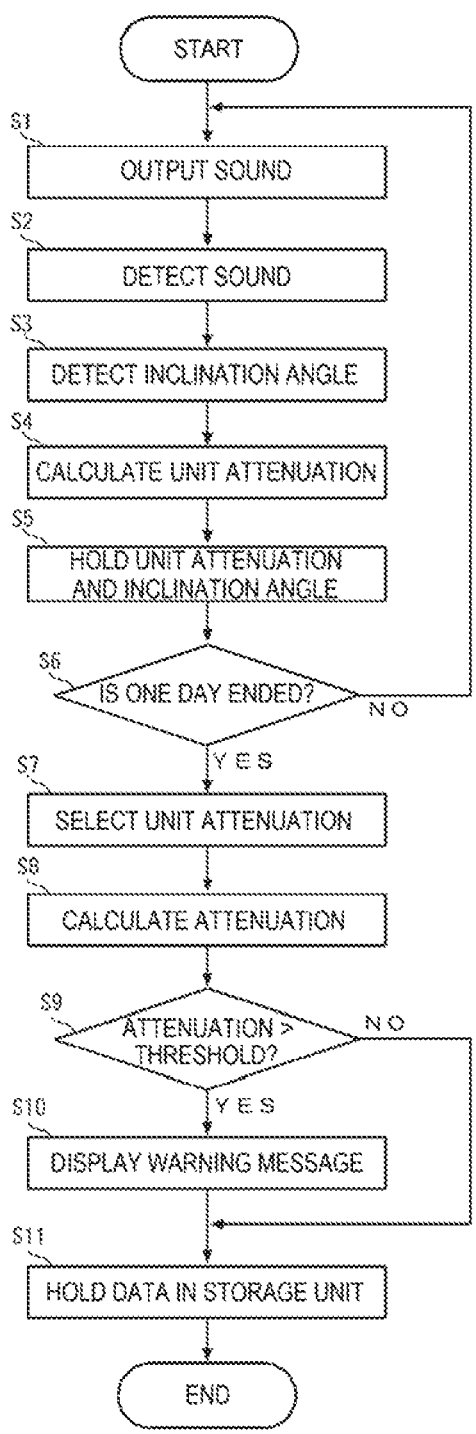
FIG. 4 is a flowchart illustrating a flow of control for the pulmonary function measurement device.

Next, a measurement method using the pulmonary function measurement device 10 according to the present embodiment will be described with reference to a flowchart illustrated in FIG. 4.

A measurement subject firstly fixes (i.e., attaches) the sound output units 20 respectively to the parts of the body surface on the rear side of the left and right lungs L, as illustrated in FIGS. 2 and 3. The measurement subject then fixes (i.e., attaches) the sound detection units 30 respectively to the parts of the body surface on the front side of the left and right lungs L. The measurement subject fixes the angle detection unit 110 at a place where the long axis of the body can be detected. The sound output unit 20 and the sound detection unit 30 are fixed to positions near the same rib R. The measurement subject then operates the input unit 70 of the device main body 90, and inputs a parameter such as the measurement time to start the measurement.

The control unit 50 starts the measurement after having received information indicating that the measurement is started from the input unit 70. Accordingly, the measurement unit 51 in the control unit 50 sends a signal to the sound output unit 20, and causes the sound output unit 20 to output a sound for a predetermined sampling period (Step 1). The measurement unit 51 then receives a detection result from the sound detection unit 30 (Step 2). The measurement unit 51 then receives a detection result of the inclination angle θ from the angle detection unit 110 (Step 3). The measurement unit 51 subsequently calculates a unit attenuation in the rib R in each of the left and right lungs L (Step 4). Thereafter, the measurement unit 51 causes the storage unit 40 to store the unit attenuation, the inclination angle θ, and the time t when the measurement is performed (Step 5). The control unit 50 stops, when predetermined measurement time is elapsed, the output of the sound from the sound output unit 20, and stops the detections by the sound detection unit 30 and the angle detection unit 110 (Step 6).

The attenuation calculation unit 52 then reads the unit attenuation, the inclination angle θ, and the time t when the measurement is performed that are stored in the storage unit 40. The attenuation calculation unit 52 specifies time t at which the inclination angle θ is within the predetermined range, and selects a unit attenuation corresponding to the time t (Step 7). Subsequently, the attenuation calculation unit 52 averages a plurality of the selected unit attenuations to calculate the attenuation V (Step 8).

Figure 5:
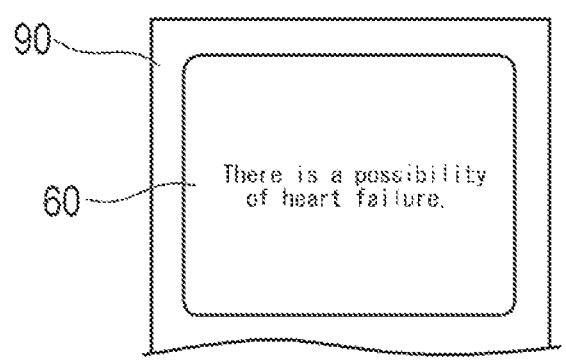
FIG. 5 is a plan view illustrating a display unit on which a warning message is displayed.

The warning determination unit 53 then determines whether the attenuation V of the day calculated by the attenuation calculation unit 52 is normal (Step 9). In a case where the warning determination unit 53 determines that the attenuation V is abnormal, the warning determination unit 53 causes the display unit 60 to display a warning message as illustrated in FIG. 5 (Step 10). Thereafter, the control unit 50 causes the storage unit 40 to store the calculated unit attenuation, the calculated attenuation V, the inclination angle θ, the presence or absence of the abnormality, and the like (Step 11). This completes the measurement for one day by the pulmonary function measurement device 10. Note that, the content of the warning message can be set as appropriate.

Figure 6:
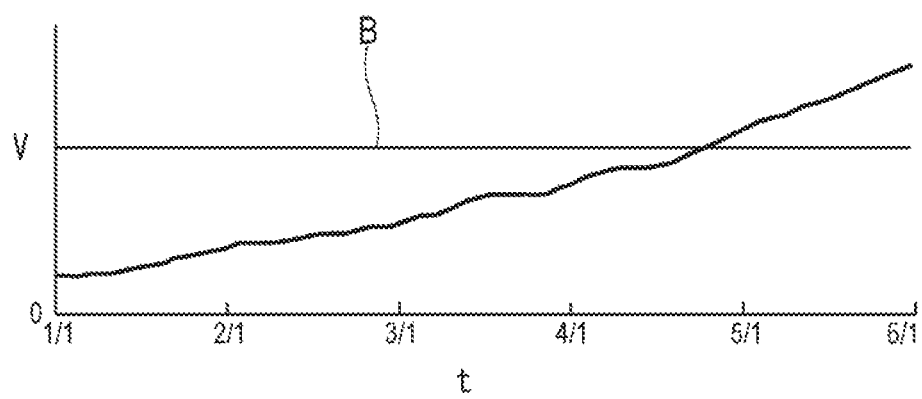
FIG. 6 is a graph illustrating a day-to-day change in attenuation calculated by the pulmonary function measurement device.

The control unit 50 can cause the display unit 60 to display a time change of the measured attenuation V with past data, as illustrated in FIG. 6. The control unit 50 can display an upper limit B (threshold) for the normal value of the attenuation V as a line on the graph that the display unit 60 is caused to display. In this graph, when the attenuation V becomes higher than the upper limit B, it is determined that there is a heart failure or there is a possibility of a heart failure. In this manner, the measurement subject himself/herself can rather easily monitor the degree of the progression of the heart failure over the long term, using the attenuation V as an index indicating the decrease in the cardiac function.

As in the foregoing, the pulmonary function measurement device 10 according to the present embodiment measures data for evaluating a pulmonary function. The pulmonary function measurement device 10 includes: the sound output unit 20 that can be fixed to a part of a body surface near the rib R, and outputs a sound toward the rib R; the sound detection unit 30 that can be fixed to a part of the body surface near the rib R toward which the sound is to be output, and detects a sound that is transmitted from the sound output unit 20 through the rib R; and the attenuation calculation unit 52 that calculates the acoustic attenuation V from information on the sound output by the sound output unit 20 and the sound detected by the sound detection unit 30.

The pulmonary function measurement device 10 as described above can calculate the acoustic attenuation V of the sound that is transmitted through the rib R using the sound output unit 20 and the sound detection unit 30 being attached to the parts of the body surface. This allows the magnitude of the congestion of the lungs serving as an index of the decrease in the cardiac function to be observed with the attenuation V, so that rather easy monitoring of the cardiac function can be achieved. Moreover, the pulmonary function measurement device 10 is rather non-invasive, and can be relatively compact in size, which results in portability and operation, so that the pulmonary function measurement device 10 causes relatively less trouble in a daily life even when the relatively long-term monitoring is continued, and can place a smaller burden to a measurement subject.

Moreover, the pulmonary function measurement device 10 further includes the storage unit 40 that can store the attenuation V, so that it is possible to compare the attenuations V that are measured at different times and calculated, which allows the time change of a cardiac function to be observed, thereby achieving rather easy and relatively long-term monitoring of the cardiac function.

Moreover, the sound output unit 20 and the sound detection unit 30 can be fixed to positions of the front and the rear of the body corresponding to the same rib R, which can detect the acoustic attenuation V with the same rib R.

Moreover, the attenuation calculation unit 52 calculates a plurality of unit attenuations from sounds that are detected at different times, and determines the attenuation V as a mean value of the plurality of unit attenuations, which removes the fluctuation of measurement for every measurement, so that it is possible to obtain the attenuation V suitable for observation.

Moreover, the pulmonary function measurement device 10 further includes the warning determination unit 53 that compares the calculated attenuation V with the upper limit B (threshold), and determines whether to issue a warning. This achieves an automatic determination of the presence or absence of a heart failure, and makes it rather easy to monitor the presence or absence of a heart failure.

Moreover, the disclosure includes a pulmonary function measurement method for measuring data for determining the presence or absence of a heart failure. The pulmonary function measurement method includes: a step of outputting a sound from a part of a body surface near the rib R toward the rib R; a step of detecting a sound that is transmitted through the rib R from a part of the body surface near the rib R toward which the sound is output; and a step of calculating the acoustic attenuation V from information on the output sound and the detected sound.

The pulmonary function measurement method as described above can observe, with the attenuation V, the congestion of the lungs L serving as an index of the decrease in the cardiac function, so that rather easy monitoring of the cardiac function can be achieved. Moreover, the pulmonary function measurement method is non-invasive, causes relatively less trouble in a daily life even when the relatively long-term monitoring is continued, and places a relatively small burden to a measurement subject.

Moreover, the pulmonary function measurement method further includes: a step of causing the storage unit 40 to store the attenuation V; and a step of reading out, from the storage unit 40, the attenuations V that are measured at different times and calculated, and comparing the attenuations V with each other, which allows the time change of a cardiac function to be observed, thereby achieving rather easy and relatively long-term monitoring of the cardiac function.

Moreover, the pulmonary function measurement method further includes a step of fixing, before the step of outputting the sound, the sound output unit 20 and the sound detection unit 30 to positions of a front and a rear of a body corresponding to the same rib R, which can detect the acoustic attenuation V with the same rib R.

Moreover, the pulmonary function measurement method further includes a step of comparing the calculated attenuation V with the upper limit B (threshold), and determining whether to issue a warning, which achieves an automatic determination of the presence or absence of a heart failure, and makes it rather easy to monitor the presence or absence of a heart failure.

Moreover, the disclosure includes a pulmonary function measurement program executable by a computer to measure data for determining the presence or absence of a heart failure. The pulmonary function measurement program includes: a step of causing the sound output unit 20 to output a sound toward the rib R; a step of receiving a detection result from the sound detection unit 30 that detects the sound; and a step of calculating the acoustic attenuation V from information on the output sound and the detected sound.

The pulmonary function measurement program as described above can observe, with the attenuation V, the congestion of the lungs serving as an index of the decrease in the cardiac function, so that rather easy monitoring of the cardiac function can be achieved. Moreover, using the pulmonary function measurement program makes the procedure be non-invasive, so that the pulmonary function measurement program causes relatively less trouble in a daily life even when the long-term monitoring is continued, and places a relatively small burden to a measurement subject.

Moreover, the pulmonary function measurement program further includes: a step of causing the storage unit 40 to store the attenuation V; and a step of reading out, from the storage unit 40, the attenuations V that are measured at different times and calculated, and comparing the attenuations V with each other, which allows the time change of a cardiac function to be observed, thereby achieving rather easy and relatively long-term monitoring of the cardiac function.

Moreover, in the pulmonary function measurement program, the sound output unit 20 and the sound detection unit 30 are fixed to positions of the front and the rear of the body corresponding to the same rib R, which can detect the acoustic attenuation V with the same rib R.

Moreover, the pulmonary function measurement program further includes a step of comparing the calculated attenuation V with the upper limit B (threshold) set in advance, and determining whether to issue a warning, which achieves an automatic determination of the presence or absence of a heart failure, and makes it rather easy to monitor the presence or absence of a heart failure.

Note that, the disclosure is not limited to the above-described embodiment, but various changes by those skilled in the art can be made within the technical scope of the invention. For example, the housing (or device main body) may be, for example, a mobile terminal such as a smartphone or a tablet terminal and the application (program), or may be a server computer terminal connected to the Internet and the application (program). The sound output unit, the sound detection unit, and the angle detection unit may be wirelessly connected to the housing (device main body) using, for example, the communication technology, such as a near field communication (NFC) or Wi-Fi®. Moreover, the sound output unit, the sound detection unit, and the angle detection unit may be integrated with the housing (device main body). Moreover, the pulmonary function measurement device 10 is a device assumed to be used by a measurement subject himself/herself, however, may be used by a health care worker such as a doctor or a nurse for the measurement subject.

Moreover, although the measurement is performed in both of the left and right lungs L in the abovementioned embodiment, the measurement may be performed in either one of the left and right lungs L. Moreover, a plurality of the sound detection units 30 may be provided in each of the left and right lungs L. The plurality of the sound detection units 30 allow data to be complemented, in a case where one sound detection unit 30 cannot detect a sound, using the detection results by the other sound detection units 30. Moreover, no angle detection unit may be provided. Moreover, although a plurality of unit attenuations are averaged to calculate the attenuation V in the abovementioned embodiment, the unit attenuation that is a measurement value for one measurement can be set as the attenuation V. Moreover, the attenuation V is not a mean value but may be a median value or a mode value (i.e., a number or attenuation that appears most often) of a plurality of the unit attenuations.

The detailed description above describes a pulmonary function measurement device, a pulmonary function measurement method, and a pulmonary function measurement program, which are for measuring data for evaluating a pulmonary function. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A pulmonary function measurement device for measuring data for evaluating a pulmonary function, the pulmonary function measurement device comprising:
   a speaker configured to be fixed to a body surface adjacent to ribs of a living body, and to output sound toward the ribs;

a microphone configured to be fixed to the body surface of the living body adjacent the ribs toward which the sound from the speaker is output, and to detect sound that is transmitted from the speaker between the ribs;

a sensor configured to detect an angle of inclination of a longitudinal axis with respect to a horizontal plane of the living body;

a processor configured to calculate an attenuation degree of a sound output by the speaker and detected by the microphone when the detected angle of the longitudinal axis of the living body with respect to the horizontal plane of the living body satisfies a predetermined condition, the predetermined condition being the detected angle of the longitudinal axis being more than 45 degree and less than 90 degrees, wherein the processor is configured to determine the pulmonary function of the living body based upon the calculated attenuation degree; and a display configured to display the pulmonary function of the living body.

2. The pulmonary function measurement device according to claim 1, further comprising:

a memory configured to store a plurality of attenuation degrees, and to compare the plurality of attenuation degrees calculated at different times.

3. The pulmonary function measurement device according to claim 1, wherein the speaker and the microphone are configured to be fixed to positions of a front and a rear of a body corresponding to a same rib.

4. The pulmonary function measurement device according to claim 1, wherein the processor is configured to calculate a plurality of attenuation degrees from sounds detected at different times, and to determine the calculated plurality of attenuation degrees as a mean value, a median value, or a mode value of the plurality of attenuation degrees.

5. The pulmonary function measurement device according to claim 1, wherein the sound output from the speaker is at a frequency of 100 Hz to 2000 Hz (Hertz).

6. The pulmonary function measurement device according to claim 1, wherein the processor is configured to compare the calculated attenuation degree with a threshold, the threshold being set in advance in a memory, input from an input unit, or calculated from past attenuation data.

7. The pulmonary function measurement device according to claim 6, wherein the display unit is configured to display a warning when the calculated attenuation degree is larger than the threshold, which reflects that a rib is in contact with a lung of the living body.

8. A pulmonary function measurement method for measuring data for evaluating a pulmonary function, the pulmonary function measurement method comprising:

outputting a sound from a body surface adjacent to ribs of the living body;

detecting the sound that is transmitted between the ribs from the body surface adjacent the ribs toward which the sound is output;

detecting an angle of inclination of a longitudinal axis with respect to a horizontal plane of the living body;

calculating an attenuation degree based on the output sound and the detected sound when the detected angle of the longitudinal axis of the living body with respect to the horizontal plane of the living body satisfies a predetermined condition, the predetermined condition being the detected angle of the longitudinal axis being more than 45 degree and less than 90 degrees, and determining the pulmonary function of the living body based upon the calculated attenuation degree; and displaying the pulmonary function of the living body.

9. The pulmonary function measurement method according to claim 8, further comprising:

storing a plurality of attenuation degrees in a memory; and reading out, from the memory, the plurality of attenuation degrees that are calculated at different times, and comparing the plurality of attenuation degrees with each other.

10. The pulmonary function measurement method according to claim 8, further comprising:

fixing, before the outputting of the sound, a speaker and a microphone to positions of a front and a rear of a body corresponding to a same rib.

11. The pulmonary function measurement method according to claim 8, further comprising:

outputting the sound at a frequency of 100 Hz to 2000 Hz (Hertz).

12. The pulmonary function measurement method according to claim 8, further comprising:

comparing the calculated attenuation degree with a threshold, the threshold being set in advance in a memory, input from an input unit, or calculated from past attenuation data.

13. The pulmonary function measurement device according to claim 12, further comprising:

displaying on a display a result when the attenuation degree is larger than the threshold, which reflects that a rib is in contact with a lung of the living body.

14. The pulmonary function measurement method according to claim 8, further comprising:

storing the angle of inclination of the longitudinal axis with respect to the horizontal plane of the living body;

calculating a plurality of attenuation degrees; and selecting and averaging the plurality of attenuation degrees only in a case where the angle of inclination of the longitudinal axis with respect to the horizontal plane of the living body satisfies a predetermined condition.

15. The pulmonary function measurement method according to claim 8, further comprising:

calculating a plurality of attenuation degrees from sounds detected at different times, and determining the attenuation degree as a mean value, a median value, or a mode value of the plurality of attenuation degrees.

16. The pulmonary function measurement method according to claim 15, further comprising:

storing the plurality of attenuation degrees, the angle of inclination for each of the plurality of attenuation degrees, and a presence or an absence of an abnormality of each of the plurality of attenuation degrees.

17. The pulmonary function measurement method according to claim 8, further comprising:

setting a sampling period when sounds are output, the sampling period being 0.1 second to 1 second.

18. A pulmonary function measurement program stored in a non-transitory, tangible computer readable recording medium configured to be executable by a computer to measure data for evaluating a pulmonary function, the pulmonary function measurement program comprising:

causing a speaker to output a sound toward ribs;

receiving a detection result from a microphone that detects the sound; and detecting an angle of inclination of a longitudinal axis with respect to a horizontal plane of the living body;

calculating an attenuation degree based on the output sound and the detected sound when the detected angle of the longitudinal axis of the living body with respect to the horizontal plane of the living body satisfies a predetermined condition, the predetermined condition being the detected angle of the longitudinal axis being more than 45 degree and less than 90 degrees, and determining the pulmonary function of the living body based upon the calculated attenuation degree; and displaying the pulmonary function of the living body.

19. The pulmonary function measurement program according to claim 18, further comprising:

storing a plurality of attenuation degrees in a memory of the computer; and reading out, from the memory, the plurality of attenuation degrees that are measured at different times and comparing the plurality of attenuation degrees with each other.

20. The pulmonary function measurement program according to claim 18, wherein the speaker and the microphone are fixed to positions of a front and a rear of a body corresponding to a same rib.

* * * * *